United States Patent [19]

Last

[11] Patent Number: 4,509,750
[45] Date of Patent: Apr. 9, 1985

[54] SURFACE VIBRATION ABSORBING STRAP

[76] Inventor: Anthony J. Last, 191 King St., Oakville, Ontario, Canada

[21] Appl. No.: 247,258

[22] Filed: Mar. 25, 1981

[30] Foreign Application Priority Data

Apr. 9, 1980 [GB] United Kingdom ................ 8011688

[51] Int. Cl.³ ............................................. A63B 69/38
[52] U.S. Cl. .......................... 273/29A; 128/DIG. 20; 128/402
[58] Field of Search ................ 273/29 A, 189, 189 A; 128/165, 75, 78, 24.2, 77, DIG. 20, 157, 402, 80 C, 80 H; 2/16, 22, 161 R

[56] References Cited

U.S. PATENT DOCUMENTS

| | | | |
|---|---|---|---|
| 2,245,909 | 10/1937 | Enfiajian | 128/DIG. 20 |
| 2,749,914 | 6/1956 | Braley | 128/402 |
| 2,943,859 | 7/1960 | Koski et al. | 128/165 X |
| 3,149,943 | 9/1964 | Amador | 128/402 |
| 3,506,013 | 4/1970 | Zdenek | 128/402 |
| 3,561,435 | 2/1971 | Nicholson | 128/DIG. 20 |
| 3,631,854 | 1/1972 | Fryer | 128/DIG. 20 |
| 3,678,936 | 7/1972 | McCormick | 128/402 |
| 3,703,171 | 11/1972 | Schiavitto | 128/8 C |
| 3,736,769 | 6/1973 | Petersen | 128/402 |
| 3,831,467 | 8/1974 | Moore | 128/80 C |
| 3,900,035 | 8/1975 | Welch | 128/402 |
| 4,044,773 | 8/1977 | Baldwin | 128/402 |
| 4,116,236 | 9/1978 | Albert | 128/8 C |
| 4,204,543 | 5/1980 | Henderson | 128/402 |

Primary Examiner—Richard C. Pinkham
Assistant Examiner—T. Brown
Attorney, Agent, or Firm—Sim & McBurney

[57] ABSTRACT

A method and device for the prevention of and the treatment for epicondylalgia externa, popularly known as Tennis Elbow, is disclosed. The method involves the absorption and dissipation of the vibrational shocks caused by the off-center hitting of a tennis ball during pronation and supination of the wrist. The device employs a vibration absorbing pad covering either the extensor or flexor muscles of the forearm. The pad is tightly located against the said muscles by means of an elastic tube from the wrist area to the elbow. An elastic strap, located outside the aforementioned tube around the largest diameter of the forearm and fastened by Velcro or like fasteners, is an additional member for maintaining the pad in close contact with the arm surface. The aforementioned pad, shaped to conform with the extensor or flexor muscle in the forearm, is filled with a viscous fluid or semi-fluid which will flow enough to maintain a close contact with the muscle from wrist to elbow. The viscous fluid absorbs the surface vibrations caused by the off-center striking of a ball with a racquet. These vibrations are normally conducted along the extensor or flexor muscles of the forearm and are a direct cause of the inflammation of the elbow itself.

8 Claims, 4 Drawing Figures

SURFACE VIBRATION ABSORBING STRAP

FIELD OF INVENTION

The present invention relates to a vibration absorbing strap for use in connection with racquet and ball game playing.

BACKGROUND TO THE INVENTION

The increased playing of tennis, squash and racquetball by men and women over 30 years of age has led to the increase of a painful problem known as "Tennis Elbow". This condition usually occurs in people between 30 and 50 years of age, where muscles and tendons have become less supple and less able to absorb and dissipate vibrational shocks.

Epicondylalgia externa (Tennis Elbow) is not only found in racquet sports but can be aggravated by other pursuits, such as, golf and bowling. It can also be found in certain trades, such as carpentry, due to repeated hammering and driving of screws, and in house painting, due to the forward and backward stroke of the brush. Also, it can be found in industrial jobs involving pneumatic hammers and the like.

The motive power that enables the forearm to be rotated from side to side comes from the wrist and not the elbow. Therefore, the start of the problem is at the wrist during pronation and supination. Shock and vibration occurring at the wrist is propagated up the extensor muscles until it terminates in the outer and supporting parts of the joint called the lateral epicondyle and also the extensor tendon that attaches the forearm extensor muscles to the epicondyle. The vibration can also be propagated up the flexor muscles in the same manner.

The forearm extensor muscles are those that come into play during the extension, raising or snapping of the wrist. Every time a tennis ball hits a racquet there is a certain force propagated up the forearm muscles which are already in tension due to the weight and acceleration of the racquet and the tension caused by the centrifugal force of the stroke. If the ball is mis-hit, an extra force is added which leads to an upward snap of the wrist. It is this extra stress that travels up the extensor muscles to the epicondyle and causes the trauma leading to inflammation. To some extent, aluminum metal or graphite racquets tend to reduce the stress because of their light weight and also racquets with oversized heads tend to reduce the problem because the larger area that the ball can hit, without twisting the racquet, reduces the number of mis-hits.

Prior art procedures to control epicondylalgia externa include tension bandages for support and non-elastic bandages which are fastened around the forearm to inhibit the massive movement of the extensor and flexor muscles and so absorb much of the shock. Further, both wrist and forearm straps which are joined by a piece of spring metal and situated either on the top or bottom of the forearm have been used. This spring metal absorbs some of the massive shock occurring in the muscles but does not absorb the surface vibrations that do much of the damage and inhibit healing of the elbow.

SUMMARY OF INVENTION

The present invention relates to the control of epicondylalgia externa in a manner superior to the prior art. In the present invention, a pad containing a viscous vibration absorbing fluid is maintained in close contact with the extensor or flexor muscles. The pad may be maintained in position by means of an elastic tube or sleeve. An elastic strap which can be tightened by Velcro fasteners or the like around the widest part of the forearm is provided to ensure close contact with the aforementioned muscles and the integrity of the device on the arm during violent exercise.

Accordingly, this invention provides a device for treating epicondylalgia externa, which comprises: pad means containing vibration-absorbing high viscosity fluid dimensioned to extend over an area of the forearm of a wearer of the device which is at least half of the area extensor or flexor muscles in the forearm projected to the forearm surface, and means for maintaining said pad means in contact with said forearm.

The device of this invention also may be used on other parts of the human frame where vibration can cause similar problems. An example is the occasional pain occurring in the lower leg, due to the vibration experienced by jogging on hard pavements.

This invention further provides for absorbing surface vibrations travelling up the extensor or flexor muscles of the forearm or other body muscles and damping the vibrations by means of a viscous fluid or semi-fluid capable of such damping.

DESCRIPTION OF PREFERRED EMBODIMENTS

Figure 1:
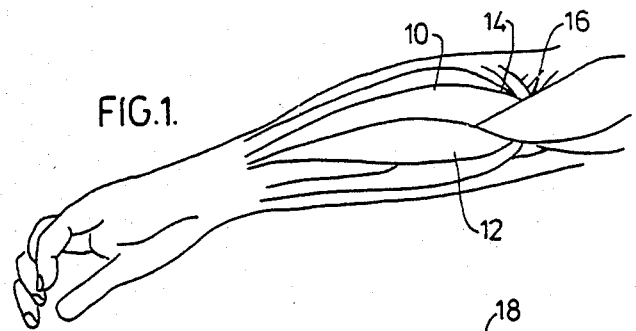
FIG. 1 is a cut-away section of a forearm showing the extensor and flexor muscles and epicondyle.
Figure 2:
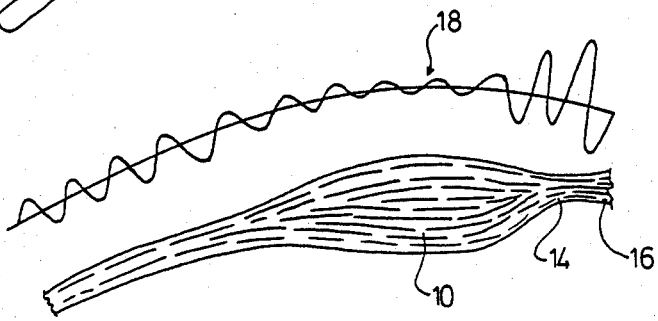
FIG. 2 is a drawing of one of the extensor muscles showing the muscle, ligament and epicondyle and the amplitude of surface vibrations occurring in the muscle.

Referring first to FIGS. 1 and 2, wherein there is illustrated the problem to which the invention relates, in FIG. 1, the numeral 10 designates the extensor group of muscles and numeral 12 the flexor group of muscles of a person's forearm. Numerals 14 and 16 designate the extensor tendon and epicondyle respectively of the extensor muscle.

In FIG. 2, only one extensor muscle 10 is shown. As in FIG. 1, numerals 14 and 16 designate the extensor tendon and epicondyle. Numeral 18 shows the amplitude of the surface vibrations as they leave the wrist area and proceed along the extensor muscles 10. They will be at their lowest amplitude at the largest cross-sectional area and, as the extensor muscle 10 necks down, so the vibration increases in amplitude to a maximum at the termination point, the epicondyle 16.

The propagation of the vibrations along the muscles is maintained until the muscle absorbs the energy and dissipates it throughout its length as heat. The muscle is itself shaped in such a way that any small vibration on its diameter rapidly increases in amplitude as the diameter becomes smaller. Those versed in the art of transmission line theory will recognize this fact and they will also recognize that, if conditions of resonance are present, the amplitudes of vibrations may become even higher. At the point where the muscle tendon 14 joins the epicondyle 16 there is an impedance change which becomes even greater at the attachment to the bone. This impedance change, which can be defined as a change in the ability to conduct or absorb vibrations, means that the energy must be released in the form of heat or strain on the epicondyle 16. It is the latter that causes the small surface tears and lesions leading to the inflammation of the epicondyle 16 and surrounding tissue.

The present invention absorbs the surface vibrations along the extensor muscles and thereby reduces the trauma at the epicondyle 16. The application of a pad of viscous vibration-absorbing fluid to the forearm increases the temperature in the muscle below the pad. The temperature increase is due to the inability of the perspiration at the skin surface to evaporate and to the friction and heat insulation of the pad itself. This increase in temperature is beneficial in that it leads to a greater absorption of vibrational energy. F. Dunn, in the Journal of the Acoustical Society of America, Volume 34, page 1545, in 1962, showed that the absorption coefficient of a vibration of 1 MHz in many types of biological tissue increases with increasing temperature.

Figure 3:
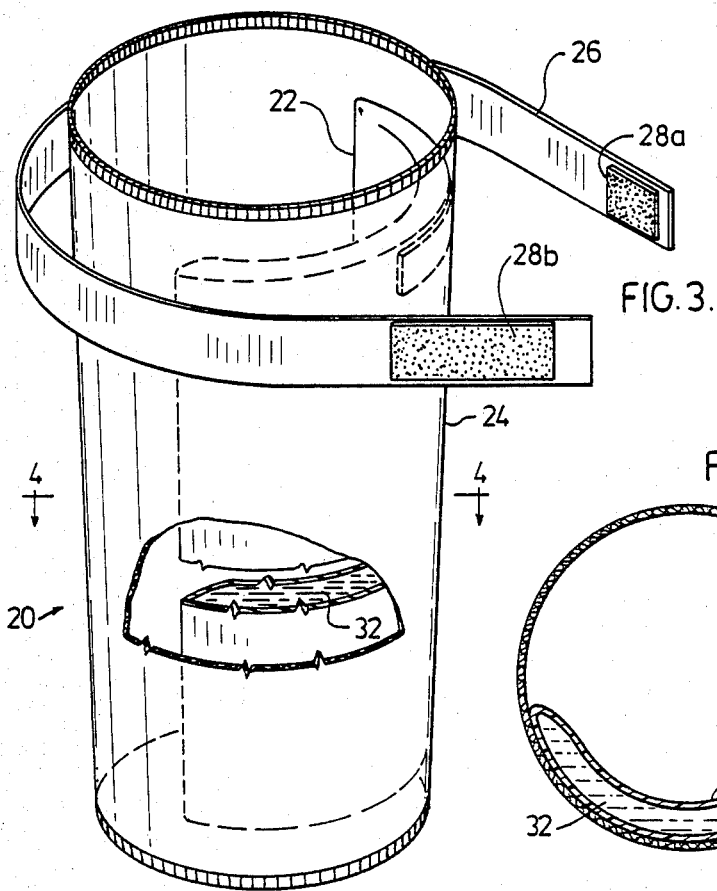
FIG. 3 is a perspective view of a device provided in accordance with a preferred embodiment of the invention.
Figure 4:
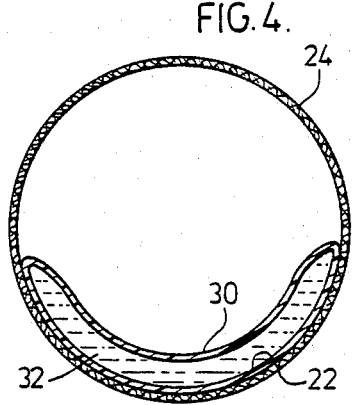
FIG. 4 is a cross-sectional view of the vibration absorbing pad of the invention at the line A—A shown in FIG. 3.

Turning now to FIGS. 3 and 4, wherein there is illustrated a preferred embodiment of the device of the invention, a device 20 comprises a vibration absorbent pad 22 filled with viscous vibrating-absorbing fluid, which is attached by means of a fastener 23, Velcro or the like, to the inside of an elastic tube 24, which is shaped and sized to be fitted on the forearm of the user of the device 20 from the wrist to just below the joint of the elbow. The pad 22 extends for almost the whole length of the tube 24. The tube may be constructed of any convenient elastic material, such as, flexible woven or knitted elastic material, or a one-way stretch material which stretches circumferentially of the tube. Over the tube 24 at approximately the widest diameter of the forearm, elastic strap 26 is attached at one end thereof (shown detached in the drawing) and surrounds the forearm and places extra tension on the pad 22 to prevent movement thereof during violent movement of the forearm on which the device 20 is worn. The strap 26 is fastened to itself by any suitable means, such as Velcro fasteners 28a and 28b or buttons.

As may be seen from the cross-sectional view of FIG. 4, the pad 22 is a flat or slightly curved container 30, made from any suitable material, such as, heat-sealable nylon, conforming with the extensor (or flexor) muscle and extends from just above the wrist to just below the elbow. The container 30 is filled with a viscous liquid or semi-liquid 32 which will absorb vibrations. The liquid must be able to flow, so as to maintain contact with the muscles as they flex with forearm motion. The liquid may be puttylike, or may be composed of an uncured thermal setting glue or a silicone fluid.

The device 20 may be positioned on a users forearm with the pad 22 inside the forearm adjacent to the flexor muscles, or outside adjacent to the extensor muscles. Sufferers from Tennis Elbow may wear the pad during normal everyday activity. The pad 22 effectively absorbs small vibrations that tend to increase additively the inflammation of the epicondyle due to small actions, such as, lifting objects and even the action of writing. In this way, the inflamed area can get a more complete rest than is normally possible and this leads to a relief of the symptons and pain of epicondylalgia externa. The device 20 should always be worn when heavy exercise of the arm is contemplated.

SUMMARY OF DISCLOSURE

In summary of this disclosure, the present invention relates to the relief of Tennis Elbow by the use of a novel device. Other modifications may be made within the scope of the invention.

What I claim is:

1. A device for treating epicondylalgia externa, which comprises:
    pad means containing vibration-absorbing high viscosity permanently-fluid material dimensioned to extend over an area of the forearm of a wearer of the device which is at least half of the area of the extensor or flexor muscles in the forearm projected to the forearm surface,
    said high viscosity permanently-fluid material being a high viscosity liquid which is selected from the group consisting of liquid silicones and liquid uncured thermal setting glues, and
    a forearm-encircling tubular member contoured to fit over a forearm and having said pad means mounted to an internal surface theroef, whereby said pad means may be maintained in contact with the forearm, said tubular member comprising a conical sleeve constructed of a fabric which is stretchable only in the circumferential direction of said tubular member.

2. A device for treating epicondylalgia externa, which comprises:
    pad means containing vibration-absorbing high viscosity permanently-fluid material dimensioned to extend over an area of the forearm of a wearer of the device which is at least half of the area of the extensor or flexor muscles in the forearm projected to the forearm surface,
    said high viscosity permanently-fluid material being a material having a viscosity resembling that of putty, and
    a forearm-encircling tubular member contoured to fit over a forearm and having said pad means mounted to an internal surface thereof, whereby said pad means may be maintained in contact with the forearm, said tubular member comprising a conical sleeve constructed of a fabric which is stretchable only in the circumferential direction of said tubular member.

3. A device for controlling epicondylalgia externa in a person to minimize the incidence thereof or to relieve the symptoms thereof, which comprises:
    pad means containing vibration absorbing high viscosity permanently-fluid material, said high viscosity permanently-fluid material being a high viscosity liquid which is selected from the group consisting of liquid silicones and liquid uncured thermal setting glues, said pad means being dimensioned to extend over an area of the forearm of a wearer of the device which is at least half the area of extensor or flexor muscles in the forearm projected to the forearm surface, and
    means for holding and maintaining said pad means in contact with said forearm, thereby to dampen and absorb surface vibration in said extensor and flexor muscles and minimize traumatization and consequent inflammation of the epicondyle of the forearm.

4. The device of claim 3 wherein said holding means comprises a forearm encircling tubular member constructed of expandable material and contoured to fit over a forearm, and said pad means is mounted to an internal surface of said tubular member.

5. The device of claim 4 wherein said tubular member is a conical sleeve constructed of flexible woven or knitted elastic material.

6. A device for controlling epicondylalgia externa in a person to minimize the incidence thereof or to relieve the symptoms thereof, which comprises:

pad means containing vibration-absorbing high viscosity permanently-fluid material, said high viscosity permanently-fluid material being a material having a viscosity resembling that of putty, said pad means being dimensioned to extend over an area of the forearm of a wearer of the device which is at least half the area of extensor or flexor muscles in the forearm projected to the forearm surface, and means for holding and maintaining said pad means in contact with said forearm, thereby to dampen and absorb surface vibrations in said extensor and flexor muscles and minimize traumatization and consequent inflammation of the epicondyle of the forearm.

7. The device of claim 6 wherein said holding means comprises a forearm encircling tubular member constructed of expandable material and contoured to fit over a forearm, and said pad means is mounted to an internal surface of said tubular member.

8. The device of claim 7 wherein said tubular member is a conical sleeve constructed of flexible woven or knitted elastic material.

* * * * *